United States Patent [19]

Kim et al.

[11] 4,303,408
[45] Dec. 1, 1981

[54] REMOVAL OF INTERFERENTS IN ANALYTICAL ASSAYS IN A TWO PHASE INTERFERENT-REMOVAL ZONE

[75] Inventors: Sang H. Kim, Pittsford; Richard W. Spayd, Rochester, both of N.Y.

[73] Assignee: Eastman Kodak Company, Rochester, N.Y.

[21] Appl. No.: 118,706

[22] Filed: Feb. 5, 1980

[51] Int. Cl.$^3$ ............... G01N 31/00; C01G 37/00; C01G 37/08
[52] U.S. Cl. ................ 23/230 B; 23/230 R; 422/56; 422/57; 204/195 M; 204/1 T; 204/195 L
[58] Field of Search ............ 422/56, 57, 58, 69, 422/60; 23/230 B; 210/634, 638, 643; 252/303, 304, 308–311; 204/195 M, 1 T, 195 P, 195 L

[56] References Cited

U.S. PATENT DOCUMENTS

| | | | |
|---|---|---|---|
| Re. 30,125 | 10/1979 | Li et al. | 210/638 |
| 2,743,818 | 5/1956 | Higuchi | 210/634 |
| 3,092,463 | 6/1963 | Adams et al. | 422/56 |
| 3,617,546 | 11/1971 | Li et al. | 210/23 |
| 3,637,488 | 1/1972 | Li et al. | 210/23 R |
| 3,711,252 | 1/1973 | Roy | 23/230 B |
| 3,725,006 | 4/1973 | Brandstrom et al. | 210/634 |
| 3,801,466 | 4/1974 | Denny | 23/230 B |
| 3,817,831 | 6/1974 | Mancilla et al. | 210/638 |
| 4,066,403 | 1/1978 | Bruschi | 422/57 |

FOREIGN PATENT DOCUMENTS 2002514 2/1979 United Kingdom .................. 422/57

Primary Examiner—William F. Smith
Assistant Examiner—Chris Konkol
Attorney, Agent, or Firm—J. Jeffrey Hawley

[57] ABSTRACT

Novel elements for the analysis of liquids which contain interferents for an analyte assay are described. Interference is reduced in multizone elements by the presence of an interferent-removing zone between the point of introduction of the liquid and the assay-indicator zone wherein the interferent-removing zone comprises a discontinuous phase within a continuous phase. An interferent-removing material is present in the discontinuous phase and the continuous phase is permeable to the analyte, its products and/or the liquid being analyzed.

53 Claims, 3 Drawing Figures

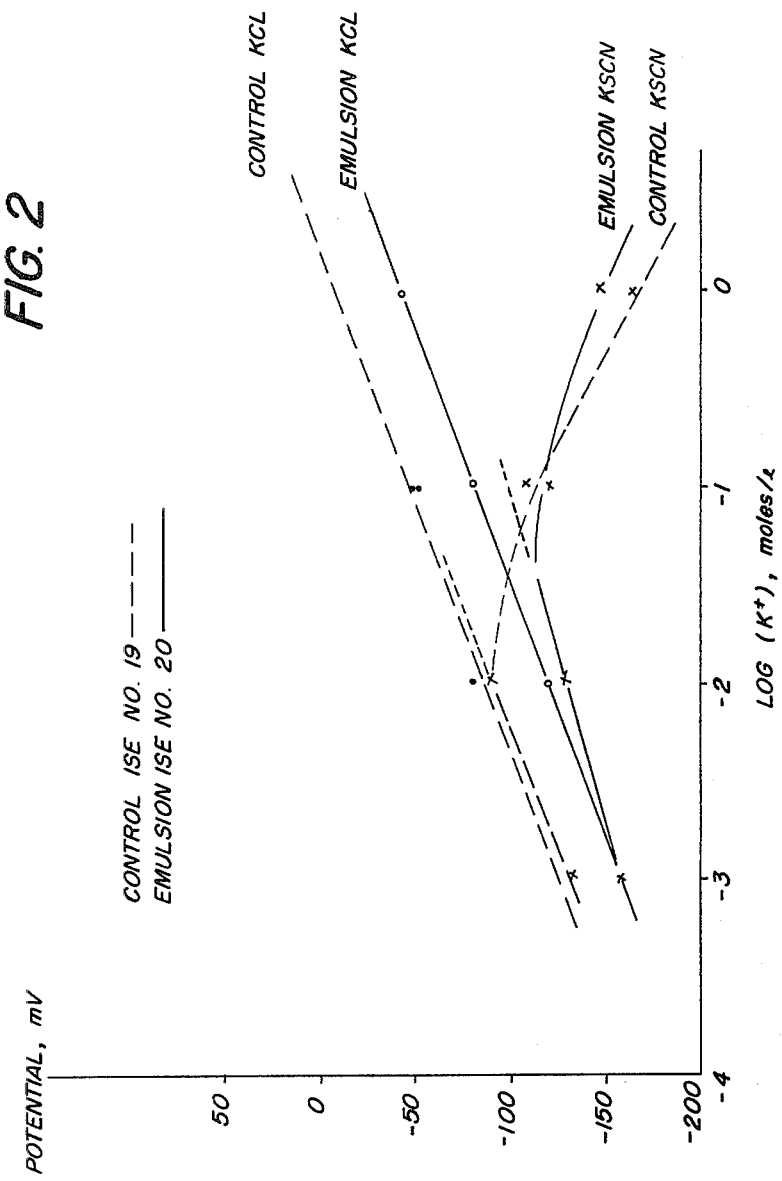

REMOVAL OF INTERFERENTS IN ANALYTICAL ASSAYS IN A TWO PHASE INTERFERENT-REMOVAL ZONE

BACKGROUND OF THE INVENTION

1. Field of the Invention

The present invention relates to the analysis of liquids which may contain interferents to the assay of the liquid under analysis.

2. Description of the Related Art

It is well known in the art to perform an analysis of a liquid by contacting that liquid with an analytical element containing either electrodes measuring the potential of or reagents capable of yielding a detectable product in proportion to the concentration of an analyte in the liquid. There are various useful methods of detecting the product, including colorimetric and potentiometric methods. The methods used can either entail the use of enzymatic reactions in liquid reagent solutions and barrel type electrodes in the ion-selective electrode method or they can be carried out in the more recent dry applications such as the multilayer element of U.S. Pat. No. 3,992,158 or the dry operative ion-selective electrode described in copending U.S. application Ser. No. 893,656 by Battaglia et al filed Apr. 5, 1978.

One particularly useful method involves an enzymatic assay wherein the analyte, upon contact with the analytical element, is oxidized in the presence of an enzyme contained therein to produce a peroxide in proportion to the concentration of the analyte in the liquid undergoing analysis. A detectable product is then produced by the reaction of the peroxide with an indicator composition in the presence of a substance having peroxidative activity. This detectable product is formed in direct proportion to the peroxide present and thus also in proportion to the concentration of the analyte. Elements and methods of this type are described in U.S. Pat. No. 3,992,158 and in U.S. Pat. No. 4,089,747 by B. J. Bruschi, both of which are incorporated herein by reference.

Methods of analyses employing reaction mechanisms other than the above-described peroxide mechanism to produce a detectable product are also known. For example, U.S. Pat. No. 3,711,252, describes a method for the quantitative analysis of uric acid in aqueous liquids wherein the aqueous liquid is contacted with a carrier element containing a ferric salt and either 2,4,6-tri(2-pyridyl)-1,3,5-triazine or 2,2':6',2"-terpyridyl, in a buffered acidic medium. A color change is produced which is directly proportional to the concentration of uric acid in the aqueous liquid.

Additional methods are described in U.S. Pat. No. 3,801,466.

Another particularly useful method includes the determination of potassium, sodium and other ions in a liquid sample using an ion-selective electrode comprising a metal/metal halide reference zone, an electrolyte layer and a membrane layer containing an ionophore for the ion to be analyzed. The potential is measured to determine concentration of the analyte. This method is described in the above-described U.S. patent application Ser. No. 893,656.

In all of the above-cited references to elements and methods for their use, it is also recognized that substances present in the liquid undergoing analysis other than the analyte may interfere with or bias the analytical reactions such that the detectable product is not formed in direct proportion to the analyte alone. This is particularly true for relatively low concentration analytes. For example, in analyzing for chloride ions using an ion-selective electrode, uric acid and bromide can interfere with the resulting potential; in potassium analysis using an ion-selective electrode, thiocyanate can interfere with the resulting potential; in the analysis of $CO_2$, gentisate and aminosalicylate interfere; in the determination of bilirubin, hemoglobin and salicylate may interfere; and in the analysis of other materials such as cholesterol, bilirubin is a known interferent.

The above interference problems are significant because these interferents are commonly found in liquids which are desirably analyzed such as blood serum and urine. Many interferents can also be present in body fluids from the ingestion of certain medications, for example, aspirin. The interferents can result in false detection of the analyte.

Methods are available and known to avoid interferences of this type. For example, U.S. Pat. No. 3,711,252, suggests prevention of gentisic acid interference by incorporation of persulfate in the analytical element. U.S. Pat. No. 3,801,466 suggests a multi-step method of avoidance involving preparation of comparative test samples in one of which the analyte is totally eliminated by a preanalysis reaction. The two samples are then analyzed for analyte, and the difference in results between the two indicates the concentration of interferents that may be present.

U.S. patent application Ser. No. 956,527 to Battaglia, Secord and Kim, filed Oct. 31, 1978, describes a method of removing uric acid and bromide ions from a potentiometric analysis of chloride ions by using an overcoat layer of a polymeric material, such as cellulose esters. The interfering bromide ions are removed by slowing down the diffusion of the interferent through the overcoat.

U.S. patent application Ser. No. 907,640 by Wu, filed May 19, 1978, describes the preparation of enzymes to degrade bilirubin and remove it as an interferent.

U.S. patent application Ser. No. 848,255 of Schubert, filed Nov. 3, 1977, describes reduction of gentisic acid interference by dissolving an indicator composition in an organic solvent.

While the above methods to alleviate interferences are useful, they are either inconvenient to use as they involve multiple steps or they are applicable to only one method of analysis.

U.S. Pat. No. 3,617,546 describes a water purification method wherein a sample of waste water is mixed in a single membrane comprising an emulsion to remove impurities. A multizone or multilayer element is not disclosed and no method of analysis is involved.

Accordingly, it would be desirable to provide an analytical element comprising multiple zones which would be effective in eliminating biases due to interferences from a variety of interferents and which would be useful for a wide variety of analytical methods.

DESCRIPTION OF THE DRAWINGS

FIG. 2 shows reduced interference using elements as described in Example 7.

SUMMARY OF THE INVENTION

Figure 1A:
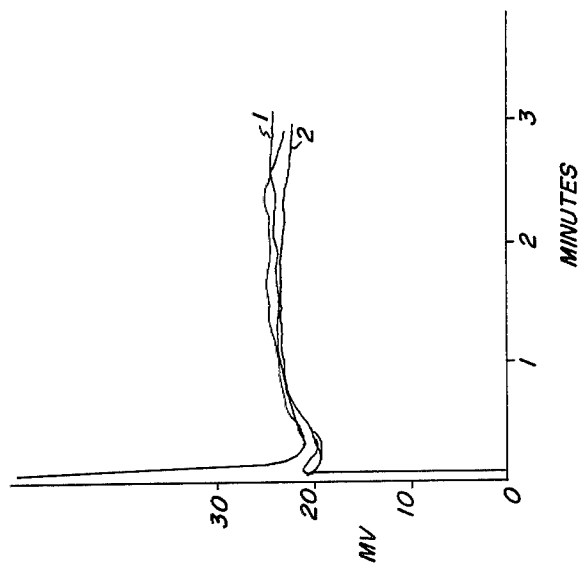
FIGS. 1A and 1B are graphs of potential vs time obtained using ion-selective electrodes as described in Example 3.

It has been found that the incorporation of dispersed two phase zones into multizoned analytical elements (including colorimetric and potentiometric), is effective in greatly reducing biases due to substances which interfere with the assay of the analyte.

The present invention provides an element for the analysis of an analyte in a liquid which may contain one or more interferents for the analysis of said analyte. The element comprises at least two zones, one zone being an interferent-removal zone and another zone being an indicator zone. The interferent-removal zone is located between the indicator zone and the point of introduction to the element of the liquid containing the analyte to be assayed. The interferent-removal zone comprises at least two phases, one phase being a discontinuous phase within a second continuous phase. The discontinuous phase contains a material capable of removing one or more interferents to the assay of the analyte and the continuous phase is permeable to the liquid, the analyte or its products.

In another embodiment of the present invention, an analyte is assayed by a method comprising applying a liquid containing an analyte to be assayed to a multizone element wherein one zone is an indicator zone and another zone is an interferent-removal zone and determining the concentration of analyte. The interferent-removal zone is located between the indicator zone and the point of introduction of the liquid to the element and said zone comprises a discontinuous phase within a continuous phase, said discontinuous phase containing a material capable of removing at least one interferent to the assay of the analyte and said continuous phase being permeable to the liquid, analyte to be assayed or its products.

The above element and method can be used to assay many analytes containing an interferent to the assay and achieve limited bias due to interference.

DESCRIPTION OF THE PREFERRED EMBODIMENT

The present invention is applicable to many kinds of analytical elements. The element is a multizone element comprising at least one indicator zone and one interferentremoval zone. The element can be one which is useful in a reaction sequence wherein the analyte reacts with reagents to provide a detectable product or with an ion-selective electrode wherein the potential of the analyte is determined.

By "multizone" element it is meant that the element comprises more than one distinct portion through which the liquid containing the analyte or product thereof travels, beginning with the portion of the element first contacted by the liquid. The element can comprise a single sheet or web containing the various portions or zones adjacent to one another so that a drop of liquid can be applied to one end and can diffuse or be carried through to the other zones. This can be on a separate support or can be self-supporting.

The preferred multizone element is one containing a plurality of layers, one over the other, preferably on a support. In this embodiment, the liquid is applied to the top layer and goes through various other layers.

Any support can be used as long as it does not interfere with the particular method of detection being used. Preferred supports transmit electromagnetic radiation in the range of the spectrum used to determine the presence and/or concentration of the detectable species in assays calling for reactions. Various useful support layers include film-forming polymers such as cellulose acetate, poly(ethylene terephthalate) and the like. Further examples of such useful radiation-transmissive supports which can be employed in the present invention are described in U.S. Pat. No. 3,992,158.

The multizone elements are useful for the analysis of a wide variety of analytes obtained from any liquid source. Thus, the liquid source can be a solvent or an aqueous liquid. In many instances it is desirable to assay for analytes in various aqueous liquids such as water containing analytes, and body fluids such as blood, serum and the like.

Many assays capable of being carried out in a multizone element are susceptible to a biased analysis due to various interferents to the assay. For example, in peroxide-detecting assays such as glucose, cholesterol, triglycerides, uric acid, lactate, etc., the following interferents are common: proteins; ascorbic acid; fluoride; gentisic acid; etc.

Free ammonia will cause a bias in ammonia-generating assays such as blood urea nitrogen and creatinine.

Pigmented materials such as bilirubin, carotene, hemoglobin and derivatives thereof, will interfere with assays that are determined in the same wavelength regions in which the pigments absorb. pH-sensitive reactions are impaired by $CO_2$, etc. from the atmosphere.

In potentiometric assays, halides interfere with each other. Also, small molecules such as uric acid and $H_2O_2$ were found to cause biases with some halide-detecting electrodes. Cation-detecting electrodes, such as those for the determination of $Na^+$ and $K^+$, are biased by various interfering materials such as surfactants, lipoproteins, thiocyanates, etc. Anion-detecting electrodes, such as $CO_2^=$-detecting electrodes, are found to be biased by certain substances found in common medication such as salicylate, gentisic acid, probenecid, etc.

The elements of this invention are useful in alleviating bias due to the above interferents to the related assays.

The element of the present invention comprises at least two zones, one of which is an interferent-removal zone and the other an indicator zone.

The indicator zone can also be termed a registration zone and is a zone from which the detection is taken. Thus, the indicator zone can be any zone which receives reaction products or detectable species released or formed in the element or it can be an interaction zone itself wherein the interaction with the analyte takes place and the species is detected. In the case of ion-selective electrodes, the indicator zone is generally the reference electrode zone from which a potentiometric measurement is made.

Examples of indicator zones or layers can be found in U.S. Pat. No. 4,042,335 wherein the term "registration layer" is used.

"Interaction" between a suitable composition and the particular analyte is used herein to refer to chemical activity, catalytic activity as in the formation of enzymesubstrate complex, or any other form of chemical or physical interaction that can release, produce, or otherwise provide within the multizone element of the invention a species that is detectable and indicative of the presence and/or concentration of a desired analyte. The detectable species that is produced can be a radiometrically detectable species, i.e., a species that is detectable by use of electromagnetic radiation measuring techniques, sometimes referred to as radiometric techniques. Typical radiometrically detectable species include materials such as dyes which are detectable by fluorometric or colorimetric techniques.

In accordance with the above description of the indicator zone, various addenda can be used. The indicator zone can comprise chromogens such as dyes and couplers; binders such as gelatin and synthetic polymers and the like; enzymes such as oxidases, reductases, transferases and the like; and surfactants. Amounts of addendum in the indicator zone can be varied as described in U.S. Pat. No. 3,992,158.

In addition to the indicator zone, the element comprises an interferent-removal zone. This zone is located between the indicator zone and the point of introduction of the liquid containing the analyte to the element.

The interference-removal zone comprises a discontinuous phase within a continuous phase. The phases can comprise emulsions of oleophilic solvents dispersed in hydrophilic substances or emulsions of hydrophilic solvents dispersed in hydrophobic substances.

If the phases constitute an oleophilic solvent dispersed in a hydrophilic substance, the interferent being removed is preferably oleophilic. Interferents of this nature are exemplified by salicylates, gentisic acid, p-aminosalicylate, thiocyanate ($SCN^-$), tetrahexylammonium chloride ($THA^+$) and the like. For example, interference from oleophilic cations such as $THA^+$ and anions such as $SCN^-$ are reduced by using an emulsion overcoat on ion-selective electrodes for the determination of potassium and sodium. Interference from surfactants such as TX-100 and Tergitol 15-S-7 also can be reduced in potassium and sodium ion-selective electrodes. Interferences such as from triglycerides and lipoproteins can also be reduced using the multizoned elements of this invention.

Discontinuous phases comprising oleophilic solvents can comprise plasticizers such as:

(a) phthalates such as diisodecyl phthalate, bis(2-ethylhexyl) phthalate, dioctyl phthalate, dinonyl phthalate, diundecyl phthalate, didecyl phthalate, didodecyl phthalate, and dipentyl phthalate;

(b) sebacates such as bis(2-ethylhexyl)sebacate;

(c) trimellitates such as triisodecyl trimellitate and tris(2-ethylhexyl) trimellitate;

(d) phosphates such as tris(2-ethylhexyl)phosphate;

(e) glycolates such as Santicizer B-16 ® (Monsanto);

(f) adipates such as diethylhexyl adipate and diisodecyl adipate known as Morflex ® 330 (Pfizer);

(g) glutarates such as diisodecylglutarate (C. P. Hall Company);

(h) polymeric plasticizer such as Morflex ® P-50 (Pfizer);

(i) ethers such as o-nitrophenylphenyl ether and p-bromophenylphenyl ether;

(j) alcohols such as 2,4-di-n-amylphenol;

(k) amides such as diethyl lauramide;

(l) aromatic solvents such as 2-nitro-p-cymene and chlorobenzene; and (m) 4'-n-alkyl-$\alpha\alpha\alpha$-trifluoroacetophenones such as butyl, hexyl, octyl, decyl and dodecyl as the alkyl group.

The above solvents can, in some instances, comprise the sole material for extracting an interferent to the assay, but other materials can also be present such as ion exchangers or complexing agents useful for extracting oleophilic anions such as salicylate, gentisic acid, p-aminosalicylate and the like. These complexing agents include:

(a) quaternary alkyl, aryl or aralkyl ammonium, phosphonium, arsonium, stibonium or sulfonium ion salts. Specific examples include quaternary ammonium salts such as (i) trioctylpropylammonium chloride (TOPAC),
(ii) trioctylpropylammonium bromide,
(iii) trioctylpropylammonium iodide,
(iv) tridodecylmethylammonium p-toluenesulfonate,
(v) 3,4-dichlorobenzyldimethyloctadecylammonium chloride,
(vi) tricaprylmethylammonium chloride (Aliquot ® 336—General Mills),
(vii) didodecyldimethylammonium chloride,
(viii) poly(styrene-co-vinylbenzyltrihexylammonium chloride) (50:50),
(ix) tetraheptylammonium chloride,
(x) tetraheptylammonium bromide,
(xi) tetrahexylammonium chloride;

(b) long-chain primary, secondary and tertiary amines and salts thereof such as trihexylamine and its HCl salt; and (c) various cationic dyes.

Ion exchangers useful for extracting oleophilic cations include alkali metal salts of tetraaryl borons such as tetraphenylboron.

When the discontinuous phase comprises an oleophilic solvent dispersed in a hydrophilic substance (emulsion), the continuous phase can contain any hydrophilic substance, especially polymers in an aqueous solution. Water-soluble polymers useful herein include agarose, gelatin, poly(vinyl alcohol) and synthetic vinyl polymers comprising:

(a) 75 to 100 weight percent of polymerized hydrophilic monomers selected from
(i) 0 to 100, preferably 80 to 100, weight percent N-vinylpyrrolidone,
(ii) 0 to 90, preferably 15 to 90, weight percent acrylamide,
(iii) 0 to 75 weight percent N-isopropylacrylamide,
(iv) 0 to 50, preferably 15 to 45, weight percent of an acrylic acid, preferably acrylic acid of methacrylic acid,
(v) 0 to 60, preferably 10 to 50, weight percent of a hydroxyalkyl acrylate, preferably hydroxyethyl acrylate or hydroxyethyl methacrylate, and
(vi) 0 to 70, preferably 15 to 65, weight percent of a -sulfoalkyl acrylate or an N-(sulfoalkyl)acrylamide, including the alkali metal and ammonium salts thereof, such as described in U.S. Pat. Nos. 2,923,734, 3,024,221, 3,411,911, 3,506,707 and 3,547,889, preferably 2-acrylamido2-methylpropanesulfonic acid, and (b) 0 to 25, preferably 1 to 20, weight percent of an active methylene group-containing monomer such as those described in U.S. Pat. Nos. 3,459,790, 3,929,482 and 3,939,130, preferably 2-acetoacetoxyethyl methacrylate.

Specific examples include:

(a) agarose;
(b) deionized gelatin;
(c) gelatin hardened with bis(vinylsulfonylmethyl) ether;
(d) poly(vinyl alcohol);
(e) poly(vinyl pyrrolidone);
(f) poly(acrylamide-co-N-vinyl-2-pyrrolidone-co-2-acetoacetoxyethyl methacrylate) (19:80:1);
(g) poly(acrylamide-co-2-acetoacetoxyethyl methacrylate) (90:10);

(h) poly(2-hydroxyethyl methacrylate-co-2-acrylamido-2-methylpropanesulfonic acid, sodium salt) (38:62);

(i) poly(2-hydroxyethyl methacrylate-co-2-acrylamido-2-methylpropanesulfonic acid, sodium salt-co-2-acetoacetoxyethyl methacrylate) (35:55:10);

(j) polymer (i) having ratio 35:45:20;

(k) poly(2-hydroxyethyl methacrylate-co-methacrylic acid, sodium salt-co-2-acetoacetoxyethyl methacrylate (50:42:8);

(l) poly(N-isopropylacrylamide-co-2-acrylamido2-methylpropanesulfonic acid, sodium salt-co-2-acetoacetoxyethyl methacrylate) (9:82:9);

(m) poly(N-isopropylacrylamide-co-2-acrylamido-2-methylpropanesulfonic acid, sodium salt-co-2-hydroxyethyl acrylate) (43:31:26);

(n) polymer (m) having ratio 74:16:10;

(o) poly(2-hydroxyethyl acrylate-co-methacrylic acid, sodium salt-co-N-isopropylacrylamide) (37:27:36);

(p) polymer (o) having ratio 47:18:35;

(q) poly(2-hydroxyethyl acrylate-co-acrylic acid, sodium salt-co-N-isopropylacrylamide) (36:23:41; equimolar ratio);

(r) poly(2-hydroxyethyl acrylate-co-2-acrylamido-2-methylpropanesulfonic acid, sodium salt) (25:29:46);

(s) poly(2-hydroxyethyl methacrylate-co-methacrylic acid, sodium salt-co-methacrylamide-co-2-acetoxyethyl methacrylate) (28:34:28:10);

(t) poly(2-hydroxyethyl acrylate-co-2-acrylamido-2-methylpropanesulfonic acid, sodium salt) (53:47);

(u) poly(2-hydroxyethyl acrylate-co-acrylamide-co-N-isopropylacrylamide( (30:30:40).

If the phases constitute water dispersed in a continuous phase comprising a solution of hydrophobic polymer in an organic solvent (invert emulsion), the interferent being removed is preferably a hydrophilic species such as bilirubin, hemoglobin, uric acid and the like.

The dispersed water can be the sole material for extracting interferents to the assay or the dispersed water can contain other materials for extracting interferents such as water-soluble complexing agents. Examples of water-soluble complexing agents useful herein include poly(N,N,N-trimethyl-N-vinylbenzylammonium chloride-co-styrene and the like.

Preferred water-soluble complexing agents are polymeric mordants which are polymeric quaternary ammonium or phosphonium compounds having recurring units of the structure

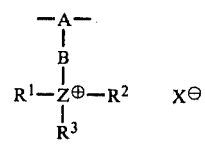

wherein
A represents a portion of a polymer backbone,
B is a linking group,
Z is

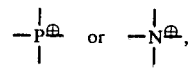

and each R group is an alkyl or an aralkyl having less than 20 carbon atoms in $R^1$, $R^2$ and $R^3$, and
X is an acid anion.

Preferred mordants also comprise 0 to 75 weight percent of additional recurring units of inert monomers such as styrene and substituted styrenes, alkyl acrylates and alkyl methacrylates; other suitable mordants may contain 0 to 5, preferably 0.5 to 2.0, weight percent of recurring units derived from difunctional monomers which crosslink to form polymers such as divinyl benzene and ethylene dimethacrylate. Specific examples are listed below.

| Mordant | Name | Structure |
|---|---|---|
| A | Poly(N,N,N-trimethyl-N-vinyl-benzylammonium)chloride | 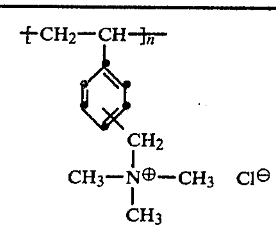 |
| B | Poly[styrene-co-benzyl(dimethyl)-p-vinylbenzylammonium chloride] | 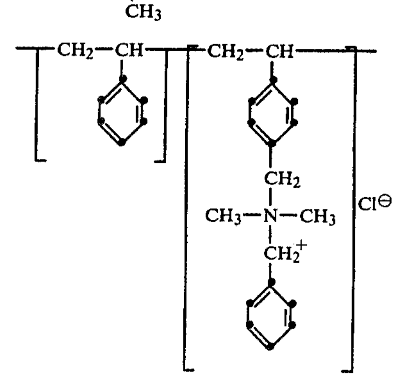 |

| Mordant | Name | Structure |
|---|---|---|
| C | Poly(N,N,N-trioctyl-N-vinyl-benzylphosphonium chloride) | 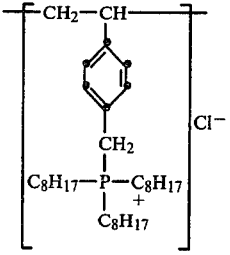 |
| D | Poly(N,N,N-trimethyl-N-vinyl benzylammonium chloride-co-styrene) | 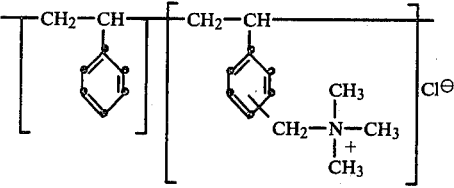 |

The continuous phase, in which the discontinuous phase comprising water is dispersed in a hydrophobic substance in an oleophilic solvent, can comprise any oleophilic solvent, examples of which are described above.

Any hydrophobic substance can be useful such as hydrophobic polymers including cellulose esters such as cellulose acetate, cellulose acetate butyrate and the like; poly(N-isopropylacrylamide) and the like.

The dispersed phases can comprise additional materials for various purposes such as surfactants such as:

(a) saponin ®;
(b) octylphenoxypolyethoxy ethanol (Triton ® X-100, Rohm and Haas);
(c) Tergitol ® 15-S-7 (Union Carbide); P (d) Zonyl FSN ® (DuPont);
(e) 10G ® (Olin Corporation);
(f) Span ® 80 (Atlas Chemical);
(g) fluorochemical surfactant FC-134 ® (3M Company);
(h) Strodex Super V8 ® (Dexter Chemical);
(i) Alkanol ® X-C (DuPont); and
(j) Surflon ® S-111 (Asahi Glass Corporation).

Other addenda include buffers, enzymes and the like.

The continuous phase of the interferent-removal zone can comprise the above components in wide ranges; the solvent or water is preferably present in a concentration of about 0.1 to about 10 g/m$^2$; the polymer is preferably present in a concentration of about 0.5 to about 30 g/m$^2$. Complexing agents, if present, are preferably present in a concentration of about 0.01 to 15 g/m$^2$ and surfactants are preferably present in a concentration of 0 to about 2 g/m$^2$.

The interference-removal zone or layer can be formed by well known processes. When the dispersed phase contains an oleophilic solvent (oil in water dispersion) the zone or layer can be formed by dissolving a complexing agent such as quaternary ammonium salt, in a water immiscible, oleophilic solvent, for example, diisodecylphthalate. If additional solubility is desired, an auxiliary solvent such as acetone, 2-butanone, methanol, isopropanol, dichloromethane or the like can be added which solvent will evaporate during drying. This solution can be added, generally with stirring, to a mixture comprised of a hydrophilic polymer, optionally a surfactant, and water. The mixture is emulsified by milling or sonifying. Addenda such as buffers can be added to the dispersions. It is noted that any other emulsion-making method known in the art can be used. The final dispersed system can be coated onto an appropriate element and dried.

When the dispersed phase contains water (water in oil emulsion), an optional complexing agent can be dissolved in water and the aqueous solution added to a mixture of hydrophobic polymer, optionally a surfactant and an oleophilic solvent. A non-aqueous coating solvent such as acetone, butanol, dichloromethane and the like can be added. The mixture is emulsified by stirring and sonifying and the final dispersion can be coated onto an element and dried.

Although the size of the particles suspended in the emulsion is not material, the finer dispersions, having more surface area, are preferred.

Analytes capable of being analyzed using the elements of the present invention include triglycerides, phospholipids, cholesterol and the like, to which the continuous phase comprising an oleophilic solvent is permeable and carbon dioxide (carbonate ion), sodium ions, potassium ions, chloride ions, glucose, uric acid, bilirubin and the like to which the continuous phase containing water is permeable.

The assay elements of this invention can be either radiometric or potentiometric elements. The various zones are preferably layers on a support and in radiometric reagent type assays can contain, in addition to the interferent-removal zone and the indicator zone, a reagent zone, a spreading zone, a radiation-blocking zone, a filtering zone, various interzones and barrier zones and the like. The potentiometric ion-selective electrodes can also contain electrolyte zones, buffer zones, membrane zones, polymeric overcoats and the like.

It is noted that the indicator zone or layer can be either integral with the element or added to the other layers or zones of the element after any interaction takes place.

Examples of preferred element formats include a support coated sequentially with an indicator layer which contains reagents to interact with either the analyte or a product thereof, an optional interlayer, the interferent-removal layer and a spreading layer.

A spreading zone or layer generally present in the area of the element closest to the introduction point of the analyte liquid as used in the multizone element of the invention may be prepared from a wide variety of materials which serve the above-described spreading function. Typically such materials include various fibrous as well as non-fibrous compositions which are porous or permeable to the particular aqueous liquid sample being analyzed. Accordingly, such layers or zones may be prepared from typical filter paper materials, various semi-permeable synthetic polymeric membranes and the like.

In accord with one preferred embodiment of the invention, the spreading zone represents a substantially non-fibrous, isotropically porous layer. Such layers can be prepared using various materials such as blushed polymer layers, optionally containing various particulate materials such as glass beads; plastic beads; pigments, e.g., titanium dioxide; particles of diatomaceous earth; microcrystalline colloidal materials, e.g., "microcrystalline cellulose"; and the like distributed therewithin. Extensive description, including methods for the preparation, of such non-fibrous, isotropically porous spreading layers may be found by reference to U.S. Pat. No. 3,992,158 referred to earlier herein. Spreading layers may be either opaque or transparent depending upon the specific materials which comprise a particular spreading layer.

Polymeric materials may be incorporated into a spreading zone or layer by impregnating the layer or zone with a solution or dispersion of the polymeric material described herein. Alternatively, the polymeric materials described for use herein may be incorporated in these compositions by incorporating the polymeric material into the coating dope or formulation from which the spreading layer or zone is prepared or cast.

Reagent zones or layers in the elements of the invention are typically radiation-transmissive, that is, they will transmit electromagnetic radiation in the range of the spectrum used to determine the presence and/or concentration of the detectable species which is formed in the multizone element as a result of interaction with the desired analyte. Typically, the reagent zone or layer is also permeable or porous to the liquid components of the aqueous sample under test and may also be porous or permeable to certain other analyte components contained in the liquid sample.

Within the reagent zone or layer is distributed a composition that can interact with the analyte, such as a proteinaceous analyte, or a reaction or decomposition product of such analyte which the particular element is designed to detect. Such interaction typically causes the formation of a detectable species or the release of a preformed detectable species contained in the reagent layer. The detectable species may be formed in the reagent zone or in the spreading zone to which precursors of the detectable species can migrate by virtue of the aqueous liquid which permeates into the reagent zone.

"Interaction" between a suitable composition and the particular analyte is used herein to refer to chemical activity, catalytic activity as in the formation of enzymesubstrate complex, or any other form of chemical or physical interaction that can release, produce or otherwise provide within the multizone element of the invention a species that is detectable and indicative of the presence and/or concentration of a desired analyte. If the detectable species that is produced is a radiometrically detectable species, i.e., a species that is detectable by use of electromagnetic radiation measuring techniques, sometimes referred to as radiometric techniques, the preferred species include materials such as dyes which are detectable by fluorometric or colorometric techniques.

The matrix of the reagent zone or layers used in the present invention in combination with the aforementioned interactive materials may be selected from a variety of materials including various fibrous materials such as filter paper materials and the like; various natural polymeric materials such as hydrophilic colloids including gelatin, agarose, polysaccharides and the like; and various synthetic polymeric materials such as poly(vinyl alcohol), poly(vinyl pyrrolidone), poly(acrylamides) and the like.

In some cases the reagent layer or zone is in itself an indicator zone since the readings are taken from that zone or layer.

U.S. Pat. No. 3,992,158 discloses extensive information regarding effective pore sizes, dry thicknesses and the like of spreading and reagent layers which can also be used in the spreading and reagent layers or zones employed in the elements of the present invention. Typically, a spreading layer having a dry thickness of from about 50 to about 300 microns and a pore size within the range of about 1 to about 100 microns, is useful in the present invention. As will be appreciated, these parameters may vary fairly widely depending upon the molecular weight and size of the particular analyte under consideration as well as the molecular weight of other components which may be present in a particular aqueous sample to be assayed. In addition, these parameters may vary significantly depending upon the composition of a spreading zone. For example, preferred nonfibrous, isotropically porous spreading layers of the type described hereinabove typically have a pore size within the range of 1 to 30 microns. However, spreading zones prepared from fibrous materials such as various filter papers and the like may differ. Representative dry thicknesses for a useful reagent layer typically are within the range of from about 10 to about 100 microns, when such layers are prepared from a matrix composed of synthetic or naturally-occurring, film-forming coated materials. However, the case wherein the matrix of a reagent layer is composed of various fibrous filter paper materials, layers having thicknesses outside this range may also be employed.

As noted hereinabove, multilayer analytical elements of the invention can also contain various additional zones or layers. Such layers can include subbing zones to aid in adhering adjacent zones of an element; registration zones to receive reaction products or detectable species released or formed in an element of the invention; radiation-blocking and reflecting zones to block and/or reflect certain wavelengths of radiation which are used to detect the presence and/or amount of a detectable species located in a particular zone of an element of the invention and the like. Methods of preparing and incorporating these zones in analytical elements of the invention are identical or similar to such methods as described in U.S. Pat. No. 3,992,158 noted above and Clement, U.S. Pat. No. 4,042,335, issued Aug. 16, 1977, both of which are incorporated herein by reference. Accordingly, extensive description of such zones is unnecessary herein. Likewise, description of various analytical procedures, including manual and automated procedures, which can employ multizone analytical elements of the present invention, are described and may be referred to in the aforementioned patents.

In another preferred embodiment, the element comprises a support having thereover, in order, a reagent-/indicator layer and a spreading layer in combination with the interferent-removal layer.

A further preferred embodiment of the present invention comprises a support having thereon sequentially, an indicator layer, a reagent layer, said interferent-removal layer and a spreading layer.

A still further preferred element comprises a support having thereon sequentially, an indicator layer, said interferent-removal layer, a reagent layer and a spreading layer.

Preferred ion-selective electrode formats include a support having thereon sequentially, a reference electrode layer such as Ag/AgCl, such as described in *Research Disclosure* No. 17638 published by Industrial Opportunities, Ltd., Homewell Havant, England (December, 1978), an electrolyte layer such as described in *Research Disclosure* No. 17638 and a membrane layer such as described in *Research Disclosure* No. 17638 and said interferent-removal layer. This format is particularly useful if potassium is the analyte wherein the liquid sample is applied to the interferent-removal layer and interferents such as $THA^+$, picrate, perchlorate, $SCN^-$ and the like are removed and the membrane contains an ionophore for potassium such as valinomycin. Copending application Ser. No. 893,656 to Battaglia et al, filed Apr. 5, 1978 now U.S. Pat. No. 4,214,968 describes the general format with the exception of the interferent-removal zone.

Another preferred ion-selective electrode format contains a support having thereon in succession, a reference element containing an electrolyte layer, a membrane layer and a layer containing both the interferent-removal zone described herein and a buffer in an amount sufficient to provide a solution having a pH of at least 7.5 when wetted with 5 microliters amount of water. This format, with the exception of the interferent-removal zone, is described in U.S. application Ser. No. 100,588 by Kim and Chang filed Dec. 5, 1979 and entitled "Buffer Overcoat for $CO_2$ Ion-Selective Electrodes" now U.S. Pat. No. 4,772,328. This format is particularly useful in the analysis of $CO_2$ or carbonate ion content.

In another preferred embodiment, an ion-selective electrode can comprise a support having thereon, in succession, a reference electrode comprising Ag/AgCl and the interferent-removal layer. This format, with the exception of the particular interferent-removal layer of this invention, is described in U.S. patent application Ser. No. 956,527 filed Oct. 31, 1978 by Battaglia, Secord and Kim now U.S. Pat. No. 4,199,412. An analysis of chloride ions is advantageously carried out using this format.

The elements of this invention can be made using any conventional coating technique well known in the art such as dip coating, curtain coating, laminating, etc.

The method of assaying involves either (1) applying a drop of the liquid to be assayed to the element and determining the concentration of the analyte by the spectrophotometric change in the indicator zone, or (2) applying a drop of the liquid to be assayed and a drop of reference fluid to the respective areas on the electrode and measuring the steady-state difference in electrical potential between the two solutions.

Typical assays that can be carried out in the former manner include reagent assays for bilirubin, cholesterol, triglycerides and the like and in the latter potentiometric assays for potassium, chloride, $CO_2$, sodium, calcium and the like.

The following examples are presented to further illustrate the present invention.

EXAMPLE 1

Reduction of Salicylate Interference in an Ion-Selective Electrode for the Determination of $CO_2$ (Buffered Aqueous Samples)

Electrode No. 1 (Control)
Electrode No. 2 (Overcoat)
Electrode No. 3 (Overcoat+Emulsion)

Dry operative ion-selective electrodes (ISE) for the determination of serum carbon dioxide* were found to exhibit large biases due to salicylate ion interference. A reduction of the salicylate bias was obtained by overcoating the electrodes with a buffer layer as described in U.S. Ser. No. 100,588. A further reduction of this interferent was obtained by the addition of the dispersed system of the present invention.

*A detailed description of the electrode can be found in U.S. patent application Ser. No. 893,656 of Battaglia et al.

To demonstrate these results, three carbonate ion-selective electrodes were prepared according to the format and methods described in the aforementioned Battaglia et al patent application Ser. No. 893,656. Electrode No. 1, comprising a membrane layer coated over a reference layer (bare electrode), was used as a control.

Electrode No. 2 was prepared in a similar manner except that it contained an overcoat comprised of 12.0 $g/m^2$ of poly(2-hydroxyethyl acrylate-co-acrylic acid, sodium salt-co-N-isopropylacrylamide) (36:23:41-equimolar ratio), and 0.12 $g/m^2$ of Surfactant 10G (a p-isononyl phenoxy polyglycidol).

Electrode No. 3 was similarly prepared except that added to the overcoat was an emulsion comprised of 3.0 $g/m^2$ of diisodecylphthalate (DIDP) and 0.8 $g/m^2$ of tricotylpropyl ammonium chloride (TOPAC).

The electrodes were tested in an absolute mode using a microreference electrode (MI-401, Microelectrodes, Inc.) and solutions containing 25 mM $NaHCO_3$ with and without 2 mM sodium salicylate (28 mg% as salicylic acid) in 0.1 M tris(hydroxymethyl)aminomethane (tris)-0.05 M HF. A 10 μl drop of each solution was spotted on the electrodes. The salicylate interference increased with time. Results, taking three minute average potentials (mV) are shown in Table I.

TABLE I

| Electrode | $\overline{mV} \pm SD$ | | | |
|---|---|---|---|---|
| | $HCO_3^-$ | $HCO_3^-$ + Salicylate | $\Delta \overline{mV}$* | % Reduction |
| No. 1 | 9.1 ± 0.14 | −77.50 ± 1.13 | −86.60 | 0 |
| No. 2 | 4.9 ± 2.62 | −28.15 ± 6.29 | −33.00 | 62% |
| No. 3 | 10.95 ± 0.35 | − 3.70 ± 2.12 | −14.65 | 83% |

*$\Delta mV = \overline{mV}$ (+salicylate) − $\overline{mV}$ ($HCO_3^-$ alone) .

As shown in Table I, incorporation of the emulsion significantly reduced the salicylate interference by greater than 80%.

EXAMPLE 2

Reduction of Salicylate Interference in an Ion-Selective Electrode for the Determination of $CO_2$ (Serum Samples)

Electrode No. 4 (Buffer)
Electrode No. 5 (Buffer + Emulsion)

Two electrodes were prepared as electrode No. 1 in Example 1. To one electrode (No. 4), a buffer overcoat was added comprising the polymer, poly(2-hydroxyethyl acrylate-co-acrylic acid, sodium salt-co-N-isopropylacrylamide) (36:23:41—equimolar ratio) (10 g/m$^2$), Surfactant 10G (0.1 g/m$^2$), tris(hydroxymethyl)aminomethane (tris) (60 mM/m$^2$) and tris-HF (tris hydrogen fluoride) (60 mM/m$^2$). The second electrode (No. 5) contained an emulsion in a buffer overcoat which was comprised of the polymer in the overcoat of electrode No. 2 (11 g/m$^2$), Surfactant 10G (0.1 g/m$^2$), tris (82 mM/m$^2$), tris-HF (82 mM/m$^2$), DIDP (3.4 g/m$^2$) and TOPAC (0.9 g/m$^2$).

The electrodes were tested as above using a human serum pool containing 25 mM $CO_2$, with and without 2 mM salicylate ions added. Results are shown in Table II.

TABLE II

| Electrode | $\overline{mV} \pm SD$ | | | |
|---|---|---|---|---|
| | No Salicylate | W/2 mM Salicylate | $\Delta \overline{mV}$ | % Reduction |
| No. 4 | 23.63 ± 0.47 | 15.73 ± 0.06 | −7.89 | 0 |
| No. 5 | 25.13 ± 0.51 | 22.27 ± 1.61 | −2.86 | 64% |

Using the buffer-overcoated electrode as the control, a 64% reduction in salicylate interference was obtained from the electrode containing the emulsion overcoat of the present invention.

EXAMPLE 3

Effect of Emulsion Overcoat on the Potentiometric Response of $CO_2$ Electrodes

A. Electrodes No. 4 and 5

The electrodes of Example 2 were used to demonstrate that the emulsion overcoat had no adverse effect on the response of the ISE.

Two human serum based calibrators containing 8.06 and 56.36 mM $CO_2$, respectively, were spotted on each of the electrodes. Results, shown in Table III, indicate that there was no adverse effect in the response to $CO_2$ when an emulsion is incorporated.

TABLE III

| Electrode | $\overline{mV} \pm SD$ | | $\Delta \overline{mV}$ | Slope mV/dec |
|---|---|---|---|---|
| | −01 | −04 | | |
| No. 4 | 32.85 ± 1.34 | 13.05 ± 0.78 | −19.80 | −23.4 |
| No. 5 | 35.15 ± 0.78 | 15.35 ± 0.07 | −19.80 | −23.4 |

B. Electrode No. 6 (Buffer)
Electrode No. 7 (Buffer + Emulsion)

Two electrodes were prepared as in Example 2 above. Electrode No. 6 was identical to electrode No. 4, i.e., contained a buffer overcoat comprised of the same components and amounts; electrode No. 7 was similar to electrode No. 5 except that it contained in the buffer overcoat an emulsion comprising DIDP (2.4 g/m$^2$) and TOPAC (0.6 g/m$^2$).

Figure 1B:
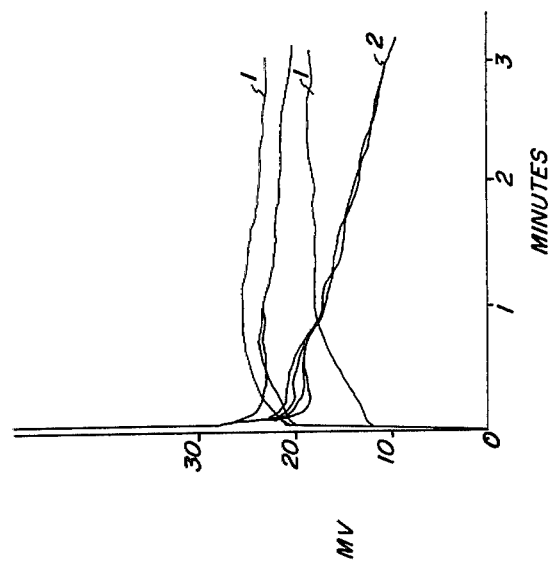

The electrodes were tested using 10 μl samples of the human serum pool mentioned above. FIG. 1A shows the potential time response obtained with electrode No. 6 comprising just a buffer overcoat (with (2) and without (1) salicylate added), and FIG. 1B shows the potential time response with electrode No. 7, i.e., elimination of the interference when the emulsion was added.

EXAMPLE 4

Comparison of Various Oil Solvents

Several emulsion-overcoated electrodes were prepared as No. 7 above, except that each contained 1.2 g/m$^2$ TOPAC and 4.8 g/m$^2$ of an oil solvent as shown in Table IV below. The electrodes were then tested as above. Comparative data, shown in Table IV, indicate that acceptable results were obtained from all of the electrodes that were tested regardless of the oil used.

TABLE IV

| Electrode No. | TOPAC g/m$^2$ | DIDP g/m$^2$ | TIDT g/m$^2$ | TEHP g/m$^2$ | BEHS g/m$^2$ | $\overline{mV} \pm SD$ (n = 3) | | $\Delta \overline{mV}$ |
|---|---|---|---|---|---|---|---|---|
| | | | | | | No Salicylate | w/2 mM Salicylate | |
| 8 | 1.2 | 4.8 | | | | 26.80 ± 1.35 | 26.40 ± 0.95 | −0.40 |
| 9 | 1.2 | | 4.8 | | | 27.30 ± 0.56 | 26.73 ± 0.86 | −0.57 |
| 10 | 1.2 | | | 4.8 | | 27.50 ± 1.61 | 27.77 ± 0.75 | +0.27 |
| 11 | 1.2 | | | | 4.8 | 25.50 ± 0.17 | 24.83 ± 0.42 | −0.67 |

TOPAC = trioctylpropylammonium chloride
DIDP = diisodecylphthalate
TIDT = triisodecyltrimellitate
TEHP = tris(2-ethylhexyl)phosphate
BEHS = bis(2-ethylhexyl)sebacate

EXAMPLE 5

Reduction of Interferences from Gentisate and p-Aminosalicylate in $CO_2$ Electrodes Electrode No. 12 (Bare)
Electrode No. 13 (Buffer)
Electrode No. 14 (Buffer + Emulsion)

Gentisate, a metabolite of aspirin and p-aminosalicylate, an antituberculin drug, were found to interfere with the $CO_2$ electrode.

Accordingly, three $CO_2$ electrodes were prepared as in Example 1. Electrode No. 12 (bare) was used as the control, electrode No. 13 contained a buffer overcoat similar to that in electrode No. 4 of Example 2 and electrode No. 14 contained an emulsion in the buffer overcoat similar to electrode No. 8, Example 4. Each electrode was tested as described above using in one case varying amounts of sodium gentisate and, in another, varying amounts of p-aminosalicylate. The control solution contained 0.02 M KHCO₃ and 0.1 M NaCl. Results are shown in Table V.

found that the addition of the emulsion overcoat of the present invention on the ISE improves the response of

TABLE V

| Electrode | | Control | 0.3 mM | 1.0 mM | 3.0 mM | 10.0 mM |
|---|---|---|---|---|---|---|
| Sodium Gentisate | | | | | | |
| 12 (Control) | $\overline{mV}$ | 5.9 | 0.6 | −4.0 | −16.6 | −40.5 |
|  | $\Delta\overline{mV}$ |  | −5.3 | −9.9 | −22.5 | −46.4 |
| % Reduction |  |  | 0 | 0 | 0 | 0 |
| 13 (Buffer) | $\overline{mV}$ | 24.7 | 23.3 | 17.8 | 7.5 | −18.0 |
|  | $\Delta\overline{mV}$ |  | −1.4 | −6.9 | −17.2 | −42.7 |
| % Reduction |  |  | 74.0 | 30.0 | 24.0 | 8.0 |
| 14 (Emul) | $\overline{mV}$ | 31.8 | 32.9 | 32.2 | 29.1 | −5.4 |
|  | $\Delta\overline{mV}$ |  | −1.1 | 0.4 | −2.7 | −37.2 |
| % Reduction |  |  | 79.0 | 96.0 | 88.0 | 20.0 |
| Sodium p-Aminosalicylate | | | | | | |
| 12 (Control) | $\overline{mV}$ | 5.9 | −0.6 | 6.9 | −2.1 | −32.7 |
|  | $\Delta\overline{mV}$ |  | −6.5 | −10.2 | −17.0 | −38.5 |
| % Reduction |  |  | 0 | 0 | 0 | 0 |
| 13 (Buffer) | $\overline{mV}$ | 24.7 | 21.1 | 21.8 | 12.3 | −9.4 |
|  | $\Delta\overline{mV}$ |  | −3.6 | −70 2.9 | −12.4 | −34.1 |
| % Reduction |  |  | 45.0 | 72.0 | 27.0 | 12.0 |
| 14 (Emul) | $\overline{mV}$ | 31.8 | 32.2 | 30.4 | 26.4 | 5.8 |
|  | $\Delta\overline{mV}$ |  | 0.4 | −1.4 | −5.4 | −26.0 |
| % Reduction |  |  | 94.0 | 86.0 | 68.0 | 33.3 |

EXAMPLE 6

Comparison of Various Ion Exchangers in the Emulsion

Several emulsion-overcoated electrodes were prepared as above except that the ion exchanger of the emulsion varied as shown in Table VI below. The electrodes were then tested as in Example 2 except that bias potentials due to 2 mM salicylate or p-aminosalicylate ions were measured differentially as described in U.S. Pat. No. 4,053,381 (Hamblen et al). The human serum pool described in Example 2 was used as the control. Comparative results, shown in Table VI, indicate that the bias reduction varied with different alkyl groups of the quaternary ammonium ions.

TABLE VI

| Electrode No. | Ion Exchanger 2.78 mmoles/m² | $\Delta\overline{mV}$ ± SD (n = 5)* Salicylate | p-Amino-salicylate |
|---|---|---|---|
| 15 | Trioctylpropyl-ammonium chloride | −0.60 ± 0.96 | −2.37 ± 1.94 |
| 16 | Tetraheptyl-ammonium chloride | −0.08 ± 1.09 | −0.64 ± 0.70 |
| 17 | Tetrahexyl-ammonium chloride | −2.43 ± 0.44 | −2.03 ± 0.97 |
| 18 | didodecyldimethyl-ammonium chloride | −5.60 ± 1.14 | −5.13 ± 1.34 |

*0 $\overline{mV}$ = no bias

EXAMPLE 7

Reduction of Thiocyanate Interference in an Electrode for the Determination of Potassium Ions Electrode No. 19 (Bare Control)
Electrode No. 20 (Emulsion Overcoat)

It is known that ion-selective electrodes for the determination of K+ based on valinomycin as the carrier exhibit interferences from oleophilic anions such as SCN− above certain levels of concentration. We have the electrode, i.e., the interference occurs at higher concentrations of SCN−.

Electrodes for the determination of K+ were prepared as described in U.S. Patent Application Serial No. 893,656 of Battaglia et al. Electrode No. 19 was used as the (bare) control; electrode No. 20 was overcoated with an emulsion comprised of 10 g/m² poly(2-hydroxyethylacrylate-co-acrylamide-co-N-isopropylacrylamide) (30:30:40 weight ratio), 2 g/m² triisodecyltrimellitate (TIDT) and 0.1 g/m² Surfactant 10G.

The electrodes were tested with two solutions, KCl and KSCN, each ranging in concentration from $10^{-3}$ M to 1.0 M. A microreference electrode (MI-401) was used as the reference. Potentials, read at three minutes, were plotted against log K+ concentrations. As shown in FIG. 2, the overcoated electrode exhibited reduced interference from both SCN− and KCl, noted by the extended linearity from $10^{-2}$ M, as achieved by the control, to $3\times10^{-2}$ M and minimized interference above that concentration.

EXAMPLE 8

Reduction of Oleophilic Cation Interferences in an Ion-Selective Electrode for the Determination of Potassium Ions Electrode No. 21 (Bare Control)
Electrode No. 22 (Emulsion Overcoat)
Electrode No. 23 (Emulsion with Na Tetraphenyl Boron)

Electrodes for the determination of K+ were prepared as above. Electrode No. 21 was similar to No. 19 of Example 7 and used as control. Electrode No. 22 was similar to No. 20 of Example 7 except that ½ the amounts were used in making the emulsion overcoat, i.e., 5 g/m² of polymer, 1 g/m² of TIDT and 0.05 g/m² of 10G. Electrode No. 23 was similar to No. 22 except that it contained, in the emulsion overcoat, 0.025 g/m² sodium tetraphenyl boron (which complexes oleophilic cations).

The electrodes were tested as above using 10 μl drops of $10^{-1}$ M KCl solutions with and without $10^{-4}$ M tetrahexyl ammonium chloride (THA+). Results, shown in Table VII, indicate that a considerable reduction in THA+ interference was obtained by using the emulsion-overcoated electrodes. Further optimization of the formulation may provide greater improvement.

TABLE VII

| Electrode No. | $\overline{\Delta mV}$* | Slope** mV/dec | Approximate Selectivity*** $K_{K+/THA+}$ | % Reduction**** |
|---|---|---|---|---|
| No. 21 (Control) | 50.4 | 43 | $1.4 \times 10^4$ | 0 |
| No. 22 (Emulsion) | 34.1 | 36 | $7.9 \times 10^3$ | 44% |
| No. 23 (Emulsion + Na Tetraphenyl Boron) | 35.1 | 41 | $6.2 \times 10^3$ | 56% |

*$\overline{mV}$ ($10^{-1}$ M KCl + $10^{-4}$ M THA+Cl−) − $\overline{mV}$ (100 mM KCl)
**$10^{-3}$ − $10^{-1}$ M KCl as determined in Example 7
***$K_{K+/THA+} \sim \dfrac{[K^+]}{[THA^+]} (10^{\Delta\overline{mV}/slope} - 1)$, where $[K^+] = 10^{-1}$ M and $[THA^+] = 10^{-4}$ M
****% reduction in the selectivity $K_{K+/THA+}$

EXAMPLE 9

Reduction of Salicylate Interference in a Multilayer Analytical Element for the Determination of Bilirubin (Colorimetric Mode)

Element No. 1 (Control)
Element No. 2 (Emulsion)

Two elements for the determination of bilirubin were prepared as follows:

Element 1 (Control)—A poly(ethylene terephthalate) film support was coated with an indicator (mordant) layer containing poly[styrene-co-vinylbenzyl)-(trihexylammonium chloride] (0.54 g/m²); a subbing layer containing poly(n-isopropylacrylamide) (1.0 g/m²) and Surfactant 10G (0.1 g/m²); and a spreading layer comprising $TiO_2$ (45.6 g/m²), cellulose acetate (6.45 g/m²), TX-405 (2.5 g/m²) and oleic ether of polyethylene glycol (0.64 g/m²).

Element 2 (Emulsion)—Element No. 2 was prepared in a similar manner except that an emulsion comprising 0.1 g/m² of TOPAC dissolved in 0.4 g/m² of DIDP was added to the subbing layer which contained poly(n-isopropylacrylamide), followed by sonication for 5–10 seconds.

The elements were tested using two human serum calibrator solutions containing 1.2 mg% and 16.1 mg% bilirubin with and without 2 mM sodium salicylate. Ten-microliter drops were spotted onto the elements, and densities ($D_R$) at 460 mμ were read at 5 minutes and 37° C. Results shown in Table VIII indicate that the salicylate interference was reduced by the emulsion.

TABLE VIII

| | $\overline{D_R} \pm$ SD (n = 3) | | |
|---|---|---|---|
| Element No. | Control | +2 mM Salicylate | Bias $\Delta D_R$ (%) |
| 1.2 mg % Bilirubin | | | |
| 1 (Control) | 0.0154 ± 0.0005 | 0.0231 ± 0.0011 | 0.0077 (50%) |
| 2 (Emulsion) | 0.0314 ± 0.0094 | 0.0353 ± 0.0067 | 0.0039 (12%) |

TABLE VIII-continued

| | $\overline{D_R} \pm$ SD (n = 3) | | |
|---|---|---|---|
| Element No. | Control | +2 mM Salicylate | Bias $\Delta D_R$ (%) |
| 16.1 mg % Bilirubin | | | |
| 1 (Control) | 0.0929 ± 0.0109 | 0.106 ± 0.0074 | 0.0131 (14%) |
| 2 (Emulsion) | 0.2590 ± 0.0210 | 0.278 ± 0.0370 | 0.0190 (7%) |

EXAMPLE 10

Reduction of Hydrophilic Interferences by Invert (Water/Oil) Emulsion Overcoats

Element No. 3 (Control)
Element No. 4

The extraction of bilirubin, known to interfere significantly with other clinical assays such as cholesterol, triglycerides, etc., demonstrates the extractive ability of the hydrophilic phase of an invert emulsion.

Analytical elements for colorimetric assays were prepared according to the following general format:

| General Format |
|---|
| Spreading Layer (Optional) |
| Invert Emulsion Layer |
| Radiation-Blocking Layer |
| Chemistry Layer(s) (Optional) |
| Registration or Indicator Layer |
| ////////// Support ////////// |

The elements of this example were prepared without spreading and chemistry layers. The chemistry or reagent layers would be those suitable for the detection of an analyte such as cholesterol, triglycerides, alkaline phosphatase or whatever assay was desired.

Elements were prepared as follows:

Element 3 (Control)—A poly(ethylene terephthalate) support was coated with a registration layer comprised of 1.15 g/m² poly(acrylamide) (A-100), and 0.05 g/m² Surfactant 10G; a radiation-blocking layer comprised of 40.0 g/m² $TiO_2$, 5.4 g/m² cellulose acetate, 1.4 g/m² Estane 57-50, 0.6 g/m² polyoxyethylene oleolether, and 1.1 g/m² surfactant TX-405; and an invert emulsion layer comprising 5.8 g/m² poly(n-isopropylacrylamide), 5.6 g/m² DIDP, 0.025 g/m² Surfactant 10G and 5.1 g/m² distilled water.

Element 4 (Invert Emulsion)—This element was prepared similarly except that the invert emulsion layer contained 0.015 g/m² of poly(N,N,N-trimethyl-N-vinylbenzylammonium chloride-co-styrene).

The elements were tested using two bilirubin calibrators shown to contain 3.0 and 16.1 mg/dl, respectively, by the KCA DuPont diazo method. Ten-microliter drops were spotted onto each element, and the reflection intensity of each was recorded after 4 minutes using a 460 mμ interference filter. From the average $\overline{mV}$ intensities of the solutions, the change in reflection density, $\Delta D_R$, was calculated and is shown in Table IX.

TABLE IX

| | $\overline{mV}$ | | |
|---|---|---|---|
| Element No. | EK-2 | Ek-8 | $\Delta D_R{}^\neq$ |
| 3 (Control) | 929 | 708 | 0.12 |

TABLE IX-continued

| Element No. | $\overline{mV}$ EK-2 | Ek-8 | $\Delta D_R{}^{\neq}$ |
|---|---|---|---|
| 4 (Invert Emulsion) | 915 | 737 | 0.09 |

$^{\neq}\Delta D_R\,(\text{EK-8}) - D_R\,(\text{EK-2}) = \log \dfrac{mV\,(\text{EK-2})}{mV\,(\text{EK-8})}$ These results indicate about a 25% reduction in $\Delta D_R$ using Element No. 4. Improved results can be expected by optimizing the amounts of the various components and coating parameters.

The invention has been described in detail with particular reference to preferred embodiments thereof, but it will be understood that variations and modifications can be effected within the spirit and scope of the invention.

What is claimed is:

1. In an element for analysis of a liquid containing an analyte wherein an interferent is removed from the assay of the analyte, said element comprising at least two zones wherein at least one zone comprises an interferent-removal zone, and at least one additional zone comprises an assay indicator zone, the improvement wherein the zone for interferent-removal comprises a discontinuous liquid phase within a continuous phase wherein the discontinuous liquid phase comprises a material for extracting an interferent to the assay of said analyte and the continuous phase is permeable to said liquid under analysis, the analyte or an interaction product, said interferent-removal zone being located between the assay indicator zone and the point of introduction of the liquid.

2. The element of claim 1 additionally comprising a support for said zones.

3. The element of claim 1 wherein each zone is a layer.

4. The element of claim 3 comprising in sequence: a support; a reagent/indicator layer; the interferent-removal layer and a spreading layer.

5. The element of claim 3 comprising in sequence: a support; a reagent/indicator layer and a spreading/interferent-removal layer.

6. The element of claim 3 comprising in sequence: a support; an indicator layer; a reagent layer; said interferent-removal layer and a spreading layer.

7. The element of claim 3 comprising in sequence: a support; an indicator layer; said interferent-removal layer; a reagent layer and a spreading layer.

8. The element of claim 3 which is an ion-selective electrode comprising in sequence: a support; a metal layer; a metal halide layer; a reference electrolyte layer; a membrane layer containing an ionophore for said analyte and said interferent-removal layer.

9. The element of claim 8 wherein said interferent-removal layer further contains a hydrophilic binder and a buffer.

10. The element of claim 3 which is an ion-selective electrode for analyzing halide comprising in sequence: a support; a metal layer; a metal halide layer and said interferent-removal layer.

11. The element of claim 1 wherein said discontinuous phase comprises an oleophilic solvent for extracting interferents to the assay of said analyte and said continuous phase comprises a hydrophilic polymer and water.

12. The element of claim 11 wherein said discontinuous phase comprises an additional material for extracting interferents to the assay of said analyte.

13. The element of claim 11 wherein said hydrophilic polymer is selected from the group consisting of agarose, gelatin, poly(vinyl alcohol) and poly(2-hydroxyethyl acrylate-co-methacrylic acid, sodium salt-co-N-isopropylacrylamide).

14. The element of claim 11 wherein said oleophilic solvent is a phthalate.

15. The element of claim 12 wherein said additional material for extracting interferents to the assay of said analyte is a complexing agent which complexes with oleophilic anions.

16. The element of claim 15 wherein said complexing agent is selected from the group consisting of quaternary alkyl, aryl or aralkyl ammonium, phosphonium, arsonium, stibonium and sulfonium ion salts.

17. The element of claim 12 wherein said material for extracting interferents to the assay of said analyte is a complexing agent which complexes with oleophilic cations.

18. The element of claim 17 wherein said complexing agent is an alkali metal salt of tetraarylboron.

19. The element of claim 1 wherein said discontinuous phase comprises water and said continuous phase comprises a hydrophobic polymer and an oleophilic solvent.

20. The element of claim 19 wherein said discontinuous phase additionally comprises another material for extracting interferents to the assay of said analyte.

21. The element of claim 19 wherein said oleophilic solvent is a phthalate.

22. The element of claim 19 wherein the hydrophobic polymer is selected from the group consisting of poly(n-isopropylacrylamide) and cellulose esters.

23. The element of claim 19 wherein said material for extracting interferents to the assay of said analyte is a water-soluble complexing agent.

24. The element of claim 23 wherein said water-soluble complexing agent is a polymeric mordant.

25. The element of claim 23 wherein said complexing agent is a polymeric quaternary ammonium or phosphonium compound having the recurring unit

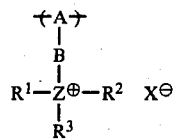

wherein:
A is a polymeric backbone;
B is a linking group;
Z is P or N;
each of $R^1$, $R^2$ and $R^3$, which are the same or different, is alkyl or aralkyl containing up to 20 carbon atoms; and
X is an anion.

26. The element of claim 25 wherein A is $CH_2-CH$.

27. The element of claim 1 wherein the assay indicator zone comprises a membrane comprising an ionophore for the analyte.

28. The element of claim 1 wherein the assay indicator zone comprises a metal halide layer.

29. The element of claim 1 wherein the continuous phase of the interferent-removal zone comprises from about 0.5 to about 30 g/m² of polymer and from about 0.1 to about 10 g/m² of oleophilic solvent or water.

30. The element of claim 29 wherein the discontinuous phase contains from about 0.01 to about 15 g/m² of material for extracting interferents to the assay of the analyte.

31. The element of claim 1 wherein the interferent-removal zone further comprises a surfactant.

32. A method for the analysis of a liquid containing an analyte in a multizone analytical element wherein at least one zone is an interferent-removal zone and at least one zone is an assay indicator zone, said method comprising:

(a) contacting the element with said liquid; and
(b) detecting in said indicator zone after a predetermined time the detectable change produced in said element, the improvement wherein said interferent-removal zone comprises a discontinuous liquid phase within a continuous phase, said discontinuous liquid phase comprising a material for extracting the interferent to the assay of said analyte and the continuous phase being permeable to said liquid under analysis, the analyte or an interaction product, said interferent-removal zone being located between the assay indicator zone and the point of contact of the element with said liquid.

33. The method of claim 32 wherein the zones are coated on a support.

34. The method of claim 32 wherein each zone is a layer.

35. The method of claim 32 wherein the element comprises in sequence: the support; a reagent/indicator layer; the interferent-removal zone and a spreading layer.

36. The method of claim 32 wherein the element comprises in sequence: a support; a reagent/indicator layer and a spreading interferent-removal layer.

37. The method of claim 33 wherein the element comprises in sequence: a support; an indicator layer; a reagent layer; said interferent-removal layer and a spreading layer.

38. The method of claim 33 wherein the element comprises in sequence: a support; an indicator layer; said interferent-removal layer; a reagent layer and a spreading layer.

39. The method of claim 33 wherein the element is an ion-selective electrode comprising in sequence: a support; a metal layer; a metal halide layer; a reference electrolyte layer; a membrane layer containing an ionophore for said analyte and said interferent-removal layer.

40. The method of claim 39 wherein said interferent-removal layer further contains a hydrophilic binder and a buffer.

41. The method of claim 33 wherein the element is an ion-selective electrode for analyzing halide ions comprising in sequence: a support; a metal layer; a metal halide layer and said interferent-removal layer.

42. The method of claim 33 wherein said liquid is a body fluid.

43. The method of claim 32 wherein said discontinuous phase comprises an oleophilic solvent as a material capable of extracting interferents to the assay of said analyte and said continuous phase comprises a hydrophilic polymer and water.

44. The method of claim 43 wherein said discontinuous phase contains an additional material for extracting interferents to the assay of said analyte.

45. The method of claim 43 wherein said material for extracting interferents to the assay of said analyte is a complexing agent which complexes with oleophilic anions.

46. The method of claim 44 wherein said material for extracting interferents to the assay of said analyte is a complexing agent which complexes with oleophilic cations.

47. The method of claim 32 wherein said discontinuous phase comprises water and said continuous phase comprises a hydrophobic polymer and an oleophilic solvent.

48. The method of claim 47 wherein said discontinuous phase comprises an additional material capable of extracting interferents to the assay of said analyte.

49. The method of claim 47 wherein said material for extracting interferents to the assay of said analyte is a water-soluble complexing agent.

50. The element of claim 1 wherein said discontinuous phase comprises an oleophilic solvent for extracting interferents to the assay of said analyte and said continuous phase comprises a hydrophilic polymer.

51. The element of claim 1 wherein said discontinuous phase comprises water and said continuous phase comprises a hydrophobic polymer.

52. The method of claim 32 wherein said discontinuous phase comprises an oleophilic solvent as a material capable of extracting interferents to the assay of said analyte and said continuous phase comprises a hydrophilic polymer.

53. The method of claim 32 wherein said discontinuous phase comprises water and said continuous phase comprises a hydrophobic polymer.

* * * * *